United States Patent [19]

Boxhoorn et al.

[11] Patent Number: 4,731,350

[45] Date of Patent: Mar. 15, 1988

[54] ETHYLENE OXIDE CATALYST

[75] Inventors: Gosse Boxhoorn; Otto M. Velthuis; Ann H. Klazinga, all of Amsterdam, Netherlands

[73] Assignee: Shell Oil Company, Houston, Tex.

[21] Appl. No.: 12,918

[22] Filed: Feb. 9, 1987

[30] Foreign Application Priority Data

Apr. 29, 1986 [GB] United Kingdom ................ 8610441

[51] Int. Cl.$^4$ ........................ B01J 21/04; B01J 23/04; B01J 23/50; B01J 27/12
[52] U.S. Cl. .................................. 502/231; 502/348; 549/534
[58] Field of Search ........................ 502/347, 348, 231

[56] References Cited

U.S. PATENT DOCUMENTS 4,010,115 3/1977 Nielsen et al. ................ 502/348 X
4,575,494 3/1986 Young et al. ........................ 502/243

*Primary Examiner*—W. J. Shine

[57] ABSTRACT

The invention relates to a process for the preparation of a silver catalyst suitable for the oxidation of ethylene to ethylene oxide, characterized in that a silver compound and, if desired, a promoter are applied to a carrier, after which the silver compound is reduced to metallic silver, and in which process the carrier has been prepared by mixing an aluminum compound with an alkali metal hydroxide and with an organic fluorine compound and by calcining the obtained mixture, to the silver catalysts prepared by means of this process and to the use of the silver catalysts in the preparation of ethylene oxide.

11 Claims, No Drawings

ETHYLENE OXIDE CATALYST

FIELD OF THE INVENTION

The invention relates to silver-containing catalysts suitable for the preparation of ethylene oxide, to the process for preparing them and to the use of the catalysts for the preparation of ethylene oxide.

BACKGROUND OF THE INVENTION

It is generally known for a silver-containing catalyst to be employed in the preparation of ethylene oxide from ethylene. See for example U.S. Pat. No. 3,962,136, issued June 8, 1976 and also the literature cited therein. In order to obtain improved silver cataysts, efforts have been directed for many years towards modifying the silver catalysts with the aid of promoters. For example, the above-mentioned U.S. Pat. No. 3,962,136 describes a process in which a silver compound is applied to a carrier, after which the applied silver compound is reduced to silver and in which additionally a promoter in the form of potassium oxide, rubidium oxide or cesium oxide or a mixture thereof is present on the carrier.

In co-pending application Ser. No. 874,913, filed June 16, 1986 is described a process for the preparation of a silver-containing catalyst suitable for the oxidation of ethylene to ethylene oxide, whereby a silver compound and, if desired, a promoter are applied to an alkali enriched carrier, after which the silver compound is reduced to metallic silver, and in which process the alkali enriched carrier has been prepared by mixing an aluminum compound with a salt of a metal of Group 1A of the Periodic System and by calcining the mixture. The obtained silver catalyst has an improved stability.

An alternative process has been found, wherein alkali enriched carrier has been prepared by mixing a hydroxide of a metal of Group 1A of the Periodic System, especially cesium hydroxide, an organic fluorine compound and an aluminum compound and by calcining the obtained mixture. The carrier is then used in the preparation of silver catalysts with improved stability.

This is surprising since alkali enriched alumina carriers, prepared with alkali metal hydroxides without the addition of an organic fluorine compound, are much less suitable for silver catalysts, since the latter have less stability.

SUMMARY OF THE INVENTION

The invention relates to a process for the preparation of a silver-containing catalyst suitable for the oxidation of ethylene to ethylene oxide, characterized in that a silver compound and, if desired, a promoter are applied to a carrier, after which the silver compound is reduced to metallic silver, and in which process the carrier has been prepared by mixing an aluminum compound with a hydroxide of a metal of Group 1A of the Periodic System and with an organic fluorine compound and by calcining the obtained mixture. The catalysts thus prepared have improved stability.

DESCRIPTION OF THE PREFERRED EMBODIMENTS

The aluminum compounds can be a variety of modifications of aluminum oxide, which when calcined at between 1200° C. and 1700° C. produce alpha-aluminum oxide, such as gamma-aluminum oxide. Another possibility is to choose a hydrated aluminum oxide, such as boehmite, which via gamma-aluminum oxide produces alpha-aluminum oxide.

The hydroxides of the metals of Group 1A of the Periodic System are lithium, sodium, potassium, rubidium or cesium. Preferably, potassium, rubidium or cesium hydroxide are used. Cesium hydroxide is particularly suitable.

The quantity of hydroxide of the alkali metal that is mixed with the aluminum compound is chosen such that the atom ratio of the metal of Group 1A/Al is between 0.0001 and 0.1, preferably between 0.001 and 0.01.

For the preparation of the alkali enriched carrier, preferably an aluminum compound is mixed with water, hydroxide of a metal of Group 1A of the Periodic System and an organic fluorine compound, the mixture thus obtained is extruded to shaped particles which are subsequently calcined. The calcination can take place in one or more steps, depending on the choice of starting material. In general, sufficient water is added to make the mixture extrudable. The extrudable applied paste obtained is then extruded in an extrusion press to form shaped pieces. These shaped pieces are heated, during which water still present is evaporated. The solid pieces are calcined. In order to prepare the alpha aluminum oxide modification, calcination up to a temperature of between 1200° C. and 1700° C. is necessary. Suitable starting materials are powders of gamma-aluminum oxide, alpha-aluminum oxide monohydrate, alpha-aluminum oxide trihydrate and beta-aluminum oxide monohydrate, which are sintered during the calcination, with fusion of the powder particles taking place. The heating and calcinating also changes the crystal structure: the cubic structure of gamma aluminum oxide changes into the hexagonal structure of alpha aluminum oxide.

The organic fluorine compound may be a fluorinated alkane, a fluorinated alkene polymer such as teflon, or a fluorinated alkane carboxylic acid, ot its salt or ester and mixtures thereof. The acid may be a monocarboxylic, a dicarboxylic or a polycarboxylic acid. Preferably the acid contains from 2 to 10 carbon atoms. Especially preferred are perfluorinated alkane monocarboxylic acids, having two to ten carbon atoms, such as trifluoro acetic acid and pentafluoro propionic acid. Generally the amount of organic fluorine compound applied is between 0.1 and 10% by weight of the mixture of alkali hydroxide and aluminum compound.

The effective catalyst surface area can vary from between 0.2 and 5 $m^2/g$. It has also been found that for the alpha-aluminum oxide, the alkali metal (cesium) is present at the surface in a concentration higher than is to be expected on the basis of the weighed-out quantity of alkali metal.

In order to prepare a catalyst, the alkali enriched carrier is then impregnated with a solution of a silver compound, sufficient to apply, as wished, 1 to 25 weight per cent of silver, calculated on the weight of the total catalyst, to the carrier. The impregnated carrier is separated from the solution and the precipitated silver compound is reduced to silver.

Preferably, a promoter is added, for example one or more of the alkali metals: potassium, rubidum or cesium. The promoters can be applied to the carrier before, during or after the impregnation with silver compound takes place. The promoter can also be applied to the carrier after the silver compound has been reduced to metallic silver.

In general, the carrier is mixed with an aqueous solution of a silver salt or silver complex, so that the carrier is impregnated with this solution, after which the carrier is separated from the solution and subsequently dried. The impregnated carrier is then heated to a temperature of between 100° C. and 400° C. for a period necessary for the silver salt (or complex) to decompose and form a finely distributed layer of metallic silver which adheres to the surfaces. A reducing or inert gas can be passed over the carrier during the heating.

Various methods are known for adding the silver. The carrier can be impregnated with an aqueous solution of silver nitrate, then dried, after which the silver nitrate is reduced with hydrogen or hydrazine. The carrier can also be impregnated with an ammoniacal solution of silver oxalate or silver carbonate, the deposition of silver metal being effected by thermally decomposing the salt. Special solutions of a silver salt with certain solubilizing and reducing agents, such as combinations of vicinal alkanolamines, alkyldiamines and ammonia also serve the purpose.

The quantity of added promoter is generally between 20 and 1000 parts by weight of an alkali metal, such as potassium, rubidium or cesium (as metal) per million parts by weight of total catalyst. 50 to 300 parts by weight of alkali metal is particularly suitable. Suitable compounds to seve as starting material for promoters are, for example, nitrates, oxalates, carboxylic acid salts or hydroxides. The most preferred promoter is cesium, the cesium being preferably employed as cesium hydroxide or cesium nitrate.

Some excellent methods are known for adding the alkali metal as promoter in which this metal can be applied at the same time as the silver. Suitable alkali metal salts are generally salts which are soluble in the silver-depositing liquid phase. Besides the above-mentioned salts, it is also worth mentioning nitrates, chlorides, iodides, bromides, bicarbonates, acetates, tartrates, lactates and isopropoxides. The use of alkali metal salts which react with the silver present in the solution and thus cause silver salts to be prematurely precipitated from an impregnating solution should, however, be avoided. For example, potassium chloride should not be used for impregnating techniques in which an aqueous silver nirate solution is used, but potassium nitrate can be used instead. Potassium chloride can be suitably used in a process in which an aqueous solution of silver amine complexes, from which no silver chloride will precipitate, is used.

In addition, the amount of alkali metal deposited on the carrier can be adjusted within certain limits by washing out a part of the alkali metal with, preferably, anhydrous methanol or ethanol. This method is employed subsequently if the concentration of the applied alkali metal is found to be too high. The temperatures, contact times and the drying with gases can be adjusted. Care should be taken to ensure that no traces of alcohol remain in the carrier.

A preferably employed process consists of the carrier being impregnated with an aqueous solution containing both alkali metal salt and silver salt, the impregnating solution being composed of a silver salt of a carboxylic acid, an organic amine, a salt of potassium, rubidum or cesium and an aqueous solvent. For example, a potassium-containing silver oxalate solution can be prepared in two ways. Silver oxide can be reacted with a mixture of ethylene diamine and oxalic acid, giving a solution containing a silver oxalate ethylene diamine complex, to which a certain amount of potassium and possible other amines such as ethanolamine is added. Silver oxalate can also be precipitated from a solution of potassium oxalate and silver nitrate, the silver oxalate thus obtained then being repeatedly washed in order to remove the attached potassium salts until the desired potassium content is obtained. The potassium-containing silver oxalate is then solubilized with ammonia and/or amine. Solutions containing rubidium and cesium can also be prepared in this way. The thus impregnated carriers are then heated to a temperature of between 100° C. and 400° C., preferably 125° C. and 325° C.

It should be noted that, irrespective of the nature of the silver in the solution before the precipitation onto the carrier, reference is always made to reduction to (metallic) silver, whereas it could also be referred to as decomposition on heating. It is preferred to think in terms of reduction, since positively charged Ag ions are converted into metallic Ag. The reduction times can be simply adapted to the starting materials employed.

As mentioned above, a promoter is preferably added to the silver. Cesium is the most preferred promoter in view of the fact that its selectivity for ethylene oxide has been found to be the highest in comparison with the use of potassium or rubidium as promoter.

A preferred catalyst comprises about 1-25 w% silver (basis total catalyst) and about 20-1000 ppm (measured as the metal, basis total catalyst) of an alkali metal promoter selected from potassium, rubidium, cesium and mixtures thereof supported on a carrier, which carrier is prepared by a process which comprises mixing an aluminum compound, preferably one selected from boehmite, gamma-aluminum and mixtures thereof with an alkali metal hydroxide, preferably cesium hydroxide, and with an organic fluorine compound, preferably a compound selected from fluorinated alkane, fluorinated alkene polymer, fluorinated alkane carboxylic acid, its salt, its ester and mixtures thereof wherein the atom ratio of alkali metal/aluminum is between about 0.0001 and about 0.1, preferably between about 0.001 and about 0.01 and calcining the resultant mixture at a temperature greater than about 1100° C., preferably between about 1200° C. and about 1700° C. In a preferred embodiment, water is also added to the mixture, which is then extruded and calcined.

The silver catalysts prepared by the process according to the present invention appear to be particularly stable catalysts for the direct catalytic oxidation of ethylene to ethylene oxide with the aid of molecular oxygen. The conditions for carrying out the oxidation reaction in the presence of the silver catalysts according to the invention are fairly similar to those already described in the literature. This applied to, for example, suitable temperatures, pressures, residence times, diluents such as nitrogen, carbon dioxide, steam, argon, methane or other saturated hydrocarbons, the presence or absence of moderating agents to control the catalytic action, for example 1,2-dichloroethane, vinyl chloride or chlorinated polyphenyl compounds, the desirability of employing either recirculating treatments of successive conversion in different reactors to enhance the yield of ethylene oxide, as well as any other special conditions which may be chosen for processes for the preparation of ethylene oxide. Usually, the pressures employed vary from about atmospheric pressure to about 35 bar. Higher pressures are, however, by no means excluded. The molecular oxygen employed as reactant can be obtained from conventional sources.

The oxygen feed can consist substantially of relatively pure oxygen, a concentrated oxygen stream consisting of a large amount of oxygen with smaller amounts of one or more diluents, such as nitrogen, argon, etc., or another oxygen-containing stream, such as air.

In a preferably employed application of the silver catalysts according to the present invention, ethylene oxide is prepared by contacting an oxygen-containing gas that has been separated from air and that contains not less than 95% oxygen with ethylene in the presence of the catalysts in question at a temperature within the range of 210° C. to 285° C. and preferably between 225° C. and 270° C.

In the reaction of ethylene with oxygen to ethylene oxide, the ethylene is present in at least a double molecular quantity, but the quantity of ethylene employed is generally much higher. The conversion is therefore calculated according to the quantity of converted oxygen in the reaction and we therefore speak of oxygen conversion. This oxygen conversion is dependent on the temperature of the reaction and is a measure of the activity of the catalyst. The values $T_{30}$, $T_{40}$ and $T_{50}$ refer to the temperatures at 30 mol%, 40 mol% and 50 mol% conversion respectively of the oxygen in the reactor. The temperatures are generally higher for a higher conversion and are highly dependent on the catalyst employed and the reaction conditions. In addition to these T-values, selectivity values are important, which indicate the molar percentage of ethylene oxide in the reaction mixture obtained. The selectivity is indicated as $S_{30}$, $S_{40}$ or $S_{50}$, which refers to the selectivity at 30%, 40% or 50% oxygen conversion respectively.

The expression "stability" of a catalyst cannot be expressed directly. Stability measurements require trials of long duration. For measuring the stability, the applicant has a number of tests wich are carried out under extreme conditions with space velocities of 30,000 liter.(liter catalyst)$^{-1}$.h$^{-1}$, where liters of throughput gas are understood to be liters STP. This space velocity is many times higher than the space velocity in commercial processes. The test is carried out for at least 1 month. The above-mentioned T- and S-values are measured during the entire period of the test. After the test has been broken off, the total quantity of ethylene oxide produced per ml catalyst is determined. The difference in selectivity and activity is calculated for a catalyst which would have produced 1000 gram ethylene oxide per ml ctalyst. A new catalyst is considered to be more stable than a known catalyst if the differences in the T- and S-values of the new catalyst are less than those of the standard catalyst which is present during each test. The stability tests are carried out at 35% oxygen conversion.

The invention is illustrated by the following examples which are provided for illustration and are not to be construed as limiting the invention.

EXAMPLE 1

0.44 Gram of cesium hydroxide dissolved in 110 ml water was mixed with 27 g Kaiser aluminum oxide ($Al_2O_3.H_2O$) by adding the aqueous cesium hydroxide solution to the aluminum oxide, and the mixture was kneaded for 5 minutes in a masticator. To this mixture was added 5 g pentafluoropropionic acid in 50 ml water and the resulting mixture was kneaded for 15 minutes. Then 108 g Kaiser aluminum oxide ($Al_2O_3.H_2O$) was added and the mixture was further kneaded for 15 minutes. The paste obtained was left to stand for three hours and then extruded. The resulting shaped pieces were dried for 1 hour at 120° C. and subsequently calcined at progressively higher temperatures. Calcination was started with the temperature rising at a rate of 200° C./h to 700° C. Calcination was then continued for 1 hour at 700° C., after which the temperature was raised in 2 hours to 1600° C. Finally, calcination was continued for 1 hour at 1600° C. The pore volume of the shaped aluminum oxide pieces was 0.50 ml.g$^{-1}$ and the average pore diameter was 0.75 μm. The resulting shaped pieces were impregnated with an aqueous solution of silver oxalate, to which cesium hydroxide was added. The impregnation was carried out for 10 minutes under vacuum, after which the shaped pieces were separated from the solution and placed in a hot air stream at a temperature of 250°–270° C. for 10 minutes in order to convert the silver salt to silver. The aqueous solution of silver oxalate was a 28 wt% Ag-containing aqueous solution in which the silver oxalate was complexed with ethylene diamine and to which solution cesium hydroxide was added. After the hot air treatment the thus impregnated shaped pieces contained 16.7 wt% Ag (calculated on total catalyst) and 490 parts by weight of cesium per million parts by weight of total catalyst.

The catalyst obtained was then tested. A cylindrical steel reactor with a length of 15 cm and a cross-section of 3 mm was filled entirely with catalyst particles of about 0.3 mm in size. The reactor was placed in a bath in which silicon/aluminum particles were present in a fluidized state. A gas mixture with the following composition was passed through the reactor: 30 mol% ethylene, 8.5 mol% oxygen, 7 mol% carbon dioxide and 54.5 mol% nitrogen and 7 parts per million parts of gas of vinyl chloride as moderator. The space velocity was 30,000 1.1$^{-1}$.h$^{-1}$. The pressure was 15 bar and the temperature was dependent on the set oxygen conversion. The measuring equipment was connected to the reactor and to a computer such that the conversion and the temperature could be accurately controlled. The concentrations of the reaction components were determined with the aid of gas chromatography and mass spectrometry. The stability test was carried out at an oxygen conversion of 35%.

The reaction temperature at 35% oxygen conversion was determined during the entire duration of the test. The selectivity in respect of ethylene oxide was also determined. After at least 30 days the test was broken off and the total quantity of ethylene oxide produced per ml catalyst was determined. From the measured reaction temperatures the temperature rise in °C. was calculated for the moment at which 1000 g ethylene oxide per ml catalyst would have been produced ($T_{35}^{1000}$). From the measured selectivities, the selectivity decrease in %mol was calculated for the moment at which 1000 g ethylene oxide per ml catalyst would have been produced ($S_{35}^{1000}$). The same measurements and calculations were carried out for a standard catalyst in the test.

The table shows the $S_{35}^{1000}$ and $T_{35}^{1000}$ in comparison with those of a standard catalyst.

| Example | Catalyst wt. % Ag | ppm Cs | $\Delta S_{35}^{1000}$ (% mol) | $\Delta T_{35}^{1000}$ (°C.) |
|---|---|---|---|---|
| 1 | 16.7 | 490 | 1.6 | 18 |
| COMP. | S839 | | 2.3 | 11 |

We claim:

1. A catalyst for the production of ethylene oxide from ethylene and molecular oxygen which comprises silver and an alkali metal promoter supported on a carrier, which carrier is prepared by a process which comprises mixing an aluminum compound with water and an alkali metal hydroxide and with an organic fluorine compound and calcining the resultant mixture at a temperature between 1200° C. and 1700° C.

2. The catalyst of claim 1 wherein the organic compound is selected from fluorinated alkane; fluorinated alkene polymer; fluorinated alkane carboxylic acid, its salt, its ester; and mixtures thereof.

3. The catalyst of claim 2 wherein the organic compound is perfluorinated alkane monocarboxylic acid having 2 to 10 carbon atoms.

4. The catalyst of claim 1 wherein the alkali metal hydroxide is cesium hydroxide.

5. The catalyst of claim 1 wherein the aluminum compound is mixed with an alkali metal hydroxide such that the atom ratio of alkali metal/aluminum is between about 0.0001 and about 0.1.

6. The catalyst of claim 5 wherein the ratio is between about 0.001 and about 0.01.

7. The catalyst of claim 1 wherein the aluminum compound is boehmite or gamma-aluminum.

8. THe catalyst of claim 1 wherein the silver comprises about 1 to about 25 %w, basis total catalyst, and the alkali metal promoter comprises about 20 to about 1000 ppm by weight of the total catalyst.

9. The catalyst of claim 1 wherein the amount of organic fluorine compound applied is between about 0.1 and about 10 percent by weight of the mixture of alkali metal hydroxide and aluminum compound.

10. The catalyst of claim 1 wherein the aluminum compound is mixed with water, the alkali metal hydroxide and the organic fluorine compound, the resulting mixture being extruded to shaped carrier particles which are then calcined.

11. A catalyst for the production of ethylene oxide from ethylene and molecular oxygen which comprises about 1-25 %wt silver (basis total catalyst) and about 20-1000 ppm (measured as the metal, basis total catalyst) of alkali metal promoter supported on a carrier, which carrier is prepared by a process which comprises mixing water and an aluminum which forms an alpha alumina upon calcination at a temperature between 1200° C. and 1700° C. with an alkali metal hydroxide and with a fluorinated alkane carboxylic acid having 2-10 carbon atoms, its salt or ester and calcining the resultant mixture at a temperature between aout 1200° C. and about 1700° C. wherein the atom ratio of alkali metal hydroxide/aluminum compound is between about 0.0001 and about 0.1 and the carboxylic acid applied is between about 0.1 and about 10 percent by weight of the mixture of alkali metal hydroxide and aluminum compound.

* * * * *